United States Patent [19]

Stendahl et al.

[11] Patent Number: 5,836,972
[45] Date of Patent: Nov. 17, 1998

[54] PARALLEL CHARGING OF MIXED CAPACITORS

[75] Inventors: Gary B. Stendahl, Crystal; James E. Brewer, St. Paul, both of Minn.

[73] Assignee: SurVivaLink Corp., Minnetonka, Minn.

[21] Appl. No.: 673,804

[22] Filed: Jun. 27, 1996

[51] Int. Cl.⁶ .................................................. A61N 1/39
[52] U.S. Cl. ................................................................ 607/5
[58] Field of Search ........................................ 607/4, 5, 7

[56] References Cited

U.S. PATENT DOCUMENTS

| | | |
|---|---|---|
| 3,857,398 | 12/1974 | Rubin . |
| 3,886,950 | 6/1975 | Ukkestad et al. . |
| 4,610,254 | 9/1986 | Morgan et al. . |
| 4,619,265 | 10/1986 | Morgan et al. . |
| 4,823,796 | 4/1989 | Benson . |
| 5,097,830 | 3/1992 | Eikefjord et al. . |
| 5,199,429 | 4/1993 | Kroll et al. ................... 607/5 |
| 5,360,435 | 11/1994 | DeGrout ....................... 607/7 |
| 5,391,186 | 2/1995 | Kroll et al. ................... 607/5 |
| 5,405,361 | 4/1995 | Persson . |
| 5,411,525 | 5/1995 | Swanson et al. .............. 607/5 |

FOREIGN PATENT DOCUMENTS

WO 95/05215  2/1995  WIPO .

OTHER PUBLICATIONS

W.A.. Tacker, Jr., "Defibrillation of the Heart", Chapter 10, pp. 196–222, Mosby–Year Book, Inc., 1994.

*Primary Examiner*—Jeffrey R. Jastrzab
*Attorney, Agent, or Firm*—Patterson & Keough, P.A.

[57] ABSTRACT

Apparatus and method for parallel charging of mixed capacitors, including a source for generating a train of high frequency pulses coupled through a pulse transformer, a high speed diode connected to the pulse transformer, a filter capacitor connected to the high speed diode and acting as a low-pass filter for the train of pulses, and a plurality of solid state switches for selectively coupling and decoupling the voltage across the filter capacitor to one of a plurality of capacitor banks which make up the biphasic high voltage defibrillation pulse supply.

23 Claims, 3 Drawing Sheets

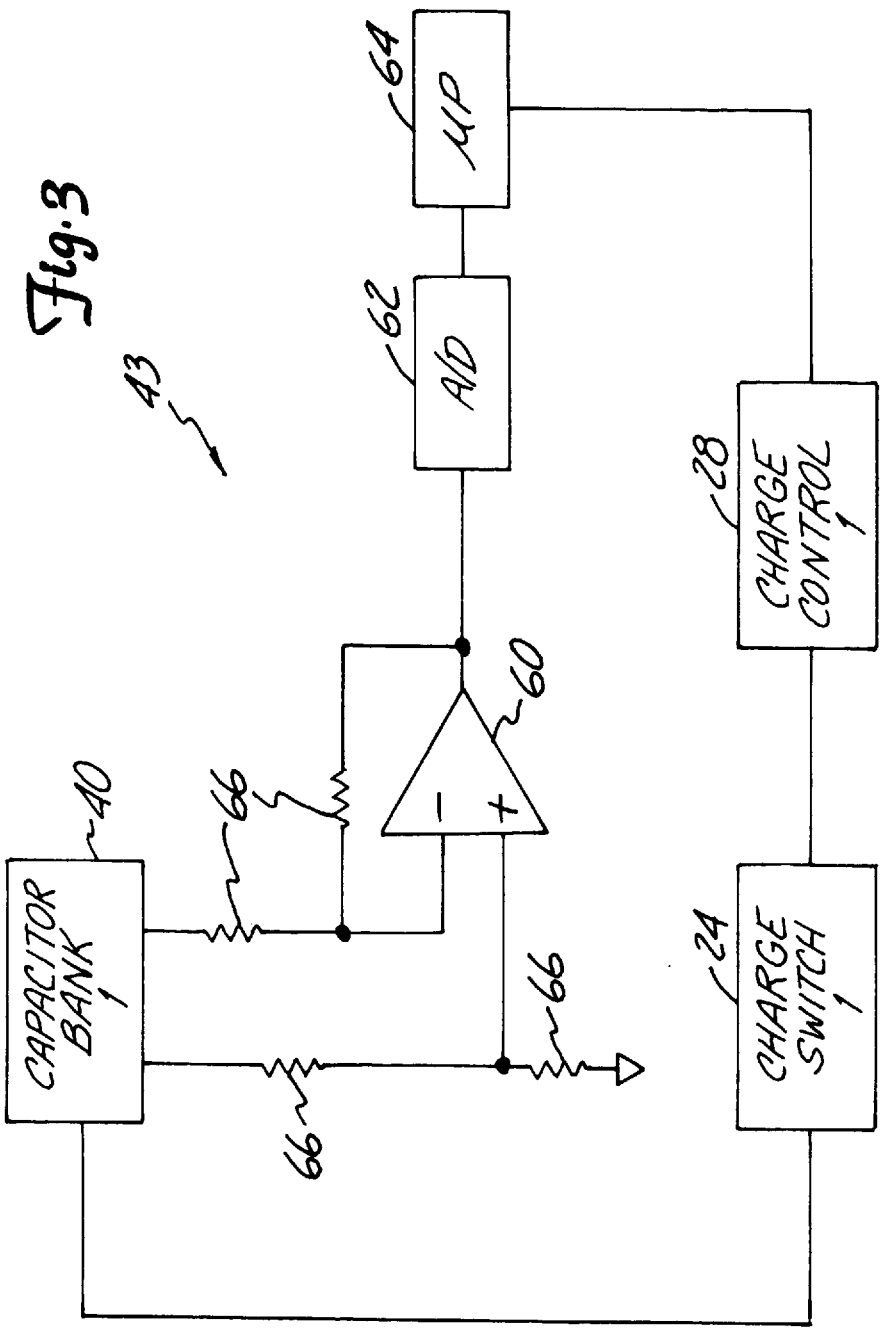

PARALLEL CHARGING OF MIXED CAPACITORS

RELATED APPLICATIONS

The present invention is related to the following co-pending U.S. Patent Applications, all of which are assigned to the assignee of the present invention and all of which are hereby incorporated by reference: High Voltage Phase Selector Switch for Defibrillators, Ser. No. 08/673,195, filed on even date herewith; Biphasic Defibrillation Isolation Circuit, Ser. No. 08/672,698, filed on even date herewith; Fast Isolated IGBT Driver for High Voltage Switching Circuit, Ser. No. 60/021,970, filed on even date herewith; and High Voltage Series Diode Circuit for Capacitor Charging, Ser. No. 60/020,714, filed on even date herewith.

BACKGROUND OF THE INVENTION

1. Field of the Invention

This invention relates to the field of external defibrillators. In particular, the present invention relates to external defibrillators capable of providing biphasic defibrillation pulses to a patient.

2. Description of the Related Art

Cardiac arrest, exposure to high voltage power lines and other trauma to the body can result in heart fibrillation which is the rapid and uncoordinated contraction of the cardiac muscle. The use of external defibrillators to restore the heartbeat to its normal pace through the application of an electrical shock is a well recognized and important tool for resuscitating patients. External defibrillation is typically used in emergency settings in which the patient is either unconscious or otherwise unable to communicate. Time is of the essence since studies have shown that the chances for successful resuscitation diminish approximately ten percent per minute.

Commercially available defibrillators such as those available from SurvivaLink Corporation, the assignee of the present application, are currently configured to produce monophasic waveform defibrillation pulses. Monophasic (i.e., single polarity) pulses such as a damped sine waveform and a truncated exponential waveform have been demonstrated to be effective for defibrillation, and meet standards promulgated by the Association for Advancement of Medical Instrumentation (AAMI). Electrical circuits for producing monophasic waveform defibrillation pulses are generally known and disclosed, for example, in the Persson U.S. Pat. No. 5,405,316 which is assigned to the assignee of the present invention and the disclosure of which is herein incorporated by reference.

The efficacy of biphasic waveform pulses (effectively two successive pulses of opposite polarities) has been established for implantable defibrillators. For example, studies conducted on implantable defibrillators have shown that biphasic waveform defibrillation pulses result in a lower defibrillation threshold than monophasic pulses. A variety of theories have been proposed to explain the defibrillation characteristics of biphasic waveform pulses but no definite conclusions have been reached.

It is anticipated that the efficacy and advantages of biphasic waveform pulses that have been demonstrated in implantable defibrillators will be demonstrated in external defibrillators as well. However, due to the voltage and current levels required in external defibrillators, typical switches suitable for handling the switching from one phase to the other of a biphasic waveform are expensive, large and fragile. For these reasons it is evident that there is a need for external defibrillators capable of producing biphasic waveform pulses in a compact, cost-effective defibrillator.

SUMMARY OF THE INVENTION

The present invention provides an external defibrillator having a high voltage circuit for delivering biphasic waveform defibrillation pulses. In the preferred embodiment of the present invention, the high voltage circuit includes first and second output terminals configured for electrical interconnection to electrodes, a supply terminal configured for electrical interconnection to a charge voltage potential, and two capacitor banks for storing electrical energy, with one bank used for the first (positive polarity) portion and the other bank for a second (negative polarity) portion of a biphasic defibrillation pulse. A pair of solid state charge switches are provided and are individually operable and responsive to charge control signals from a pair of charge control circuits to selectively electrically connect each of the capacitor banks to the pulse generator to charge the capacitor banks to a desired charge voltage potential.

BRIEF DESCRIPTION OF THE DRAWINGS

FIG. 3 illustrates one preferred embodiment of a monitoring circuit of the present invention.

DETAILED DESCRIPTION OF THE INVENTION

Figure 1:
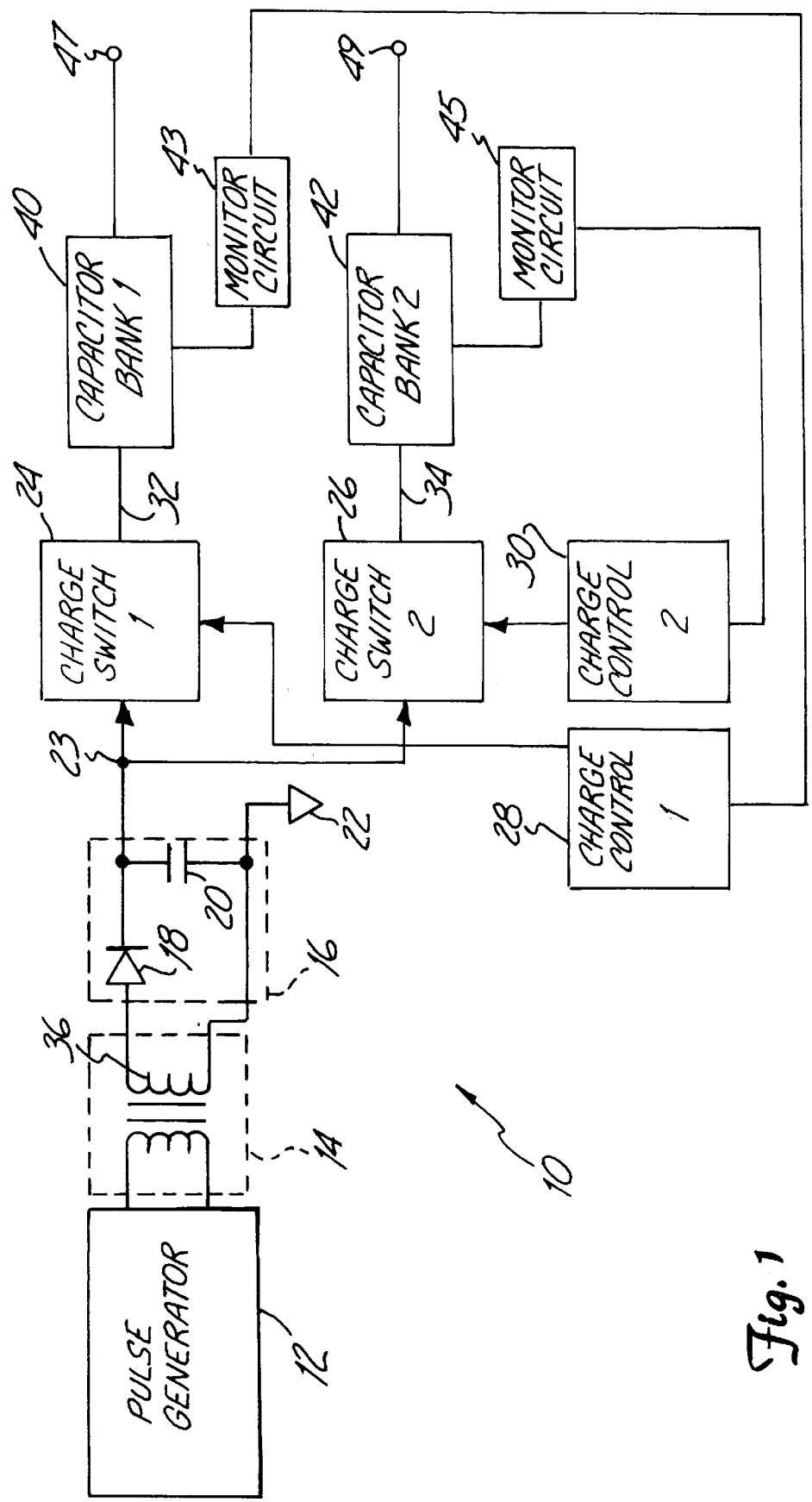
FIG. 1 is a block diagram of a capacitor charge control circuit in accordance with the present invention.

Referring now to FIG. 1, a charge control circuit 10 useful in the practice of the present invention may be seen. Circuit 10 includes a pulse generator 12 connected to a pulse transformer 14 which is connected to a passive rectifying and filtering circuit 16. Circuit 16 is preferably made up of a high speed (fast recovery) diode 18, which is preferably a UF4007 type, available from General Instruments, and a capacitor 20 which may be in the range of 3–10 microfarads. It should be noted that an active filter, which are commonly known to those skilled in the art, could be used in place of passive filter 16 without departing from the spirit or scope of the present invention. Circuit common is indicated by an inverted triangle 22, and an output 23 of the rectifying and filtering circuit 16 is connected to first and second charge switches 24, 26. Charge switches 24, 26 are each preferably formed of one or more solid state switching devices such as a silicon controlled rectifier (SCR), a field effect transistor (FET), or an isolated gate bipolar transistor (IGBT). Such devices may be connected in series (to increase voltage capability) or in parallel (to increase current capability) as is well known in the art. Each of the charge switches 24, 26 is controlled by a separate one of a pair of charge control circuits 28, 30.

The respective outputs 32, 34 of the charge switches 24, 26 are individually connected to one of a pair of capacitor banks 40, 42. Output 32 is connected to a first capacitor bank 40, and output 34 is connected to a second capacitor bank 42. The present invention will be described in detail with reference to a pair of capacitor banks but it should be noted that additional capacitor banks may also be included without departing from the spirit or scope of the present invention.

The output of capacitor bank 40 is connected to an electrode terminal 47 and the output of capacitor bank 42 is connected to an electrode terminal 49.

The circuit of the present invention is designed to output to electrode terminals 47 and 49 a high voltage defibrillation pulse in the range of approximately 2000–3000 volts in the preferred embodiment. It should be noted however that greater or lesser discharge voltages can also be delivered without departing from the spirit or scope of the present invention. In order to generate and deliver the voltage levels desired for defibrillation, a two step process is required. The first step is that of charging the capacitors. The second step is that of discharging the capacitors. To charge low cost, reliable capacitors rapidly to the desired voltage levels, the present invention utilizes charge control circuits 28, 30 and charge switch circuits 24, 26 to charge the capacitors in parallel. When connected in parallel, the total capacitance of a particular capacitance bank is the sum of all the capacitors connected in parallel, while the voltage across each of the individual capacitors is equal. To discharge the capacitors to electrode terminals 47, 49, charge control circuits 28, 30 and charge switch circuits 24, 26 configure the capacitors of a capacitor bank in series. This reduces the total capacitance to a fractional value of the individual capacitors and increase the voltage to the sum of the voltages across each individual capacitor.

The capacitor banks of the present invention are preferably of differing capacitive values or differing voltage capacities. For example, in one embodiment, capacitor bank 40 has a total capacitance of 7200 microfarads while capacitor bank 42 has a total capacitance of 440 microfarads when connected in parallel for charging. Therefore, capacitor bank 42 will charge much more rapidly than will capacitor bank 40. During discharge, capacitor bank 40 has a total capacitance of 200 microfarads while capacitor bank 42 has a total capacitance of 110 microfarads while connected in series. It should be noted that many other capacitor banks could be utilized having many different capacitance values, or all having the same capacitance value without departing from the spirit or scope of the present invention.

The operation of the charge control circuit 10 is as follows. Pulse generator 12 supplies a series, or train, of preferably square wave pulses, typically at a 50% duty cycle and having an amplitude of approximately 400 volts, at a frequency preferably between 5 KHz and 500 KHz. These pulses have a very rapid rise time. Since the fast rise times and high frequencies of the pulses cause avalanching of most common solid state devices of reasonable cost, the pulses are first passed through passive filter circuit 16. Diode 18 is a fast recovery diode that provides for charging of capacitor 20 and prevents discharge of the capacitor 20 through secondary 36 of pulse transformer 14. Capacitor 20 is preferably selected to be able to absorb and store the energy from at least one charge pulse from pulse generator 12.

As stated above, use of a pulse train with a very rapid rise time on individual pulses is desired, but would lead to avalanche breakdown of standard switches if coupled directly thereto. This would cause the switches to lose control of charging, and may lock the switches on, causing the capacitors to be continually charged until they are destroyed. This consequent loss of charging control is unacceptable. Use of rectifying and filtering circuit 16 avoids such avalanche triggering of solid state switches 24, 26 by keeping high dV/dt values from reaching switches 24, 26, allowing ordinary solid state devices to be used for switches 24, 26.

Figure 2:
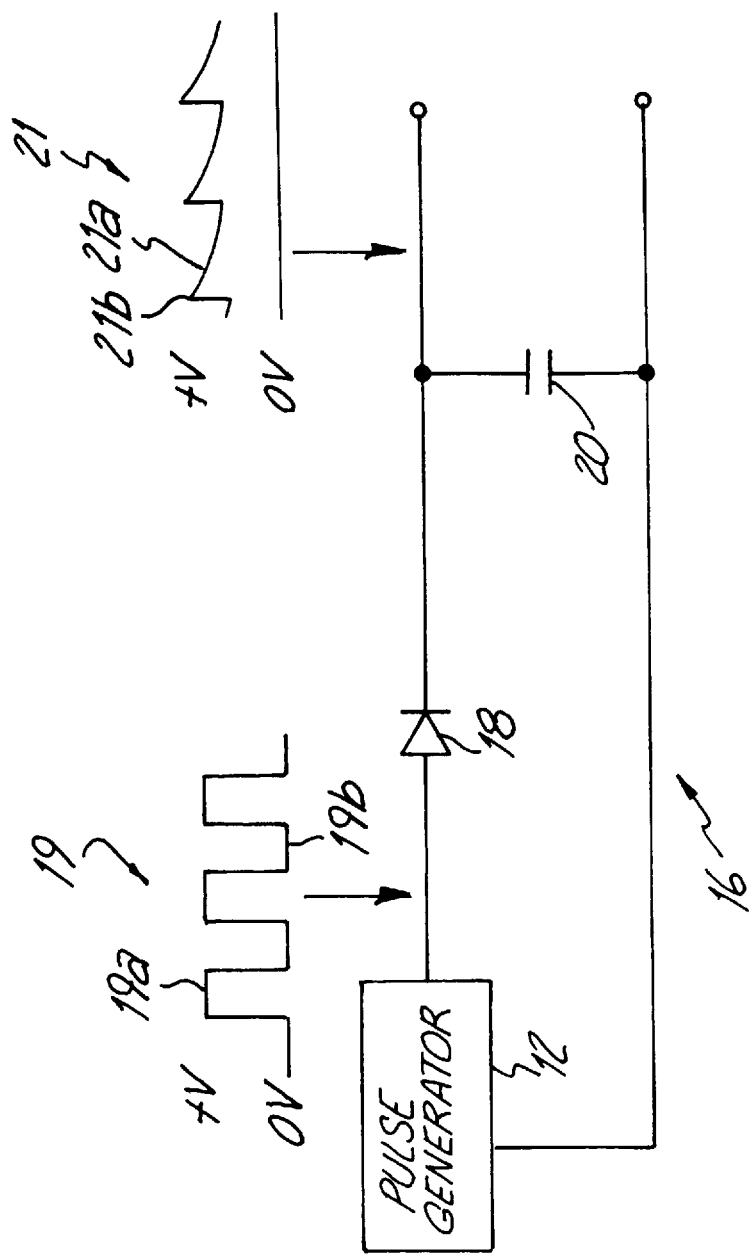
FIG. 2 illustrates a passive filter of the preferred embodiment along with a pictorial representation of a signal before and after the filter.

FIG. 2 illustrates the passive filter of the preferred embodiment along with a pictorial representation of a signal before and after the filter. As can be seen in waveform 19 illustrates the signal coming out of pulse generator 12. This signal is a series of square wave pulses having an amplitude of approximately 400 volts. After passing through filter 16, waveform 21 is obtained which is in the form of a DC level with a generally triangular ripple component. When the ON portion of waveform 19, illustrated at 19a, is seen at diode 18 the diode is forward biased allowing capacitor 20 to charge. Capacitor 20 is charged while diode 18 is forward biased. When signal 19 drops to zero, illustrated at 19b, diode 18 shuts off, halting the charging of capacitor 20. During the off period of diode 18 when the stored energy from capacitor 20 is transferred to the capacitor banks its voltage drops slightly causing the triangular ripple voltage illustrated in waveform 21 at 21a. After capacitor 20 has a chance to discharge the energy stored therein, diode 18 turns back on due to the presence again of a positive voltage from pulse generator 12 causing waveform 21 to rise to a charged level, at 21b.

The DC charge on capacitor 20 is available to each of switches 24, 26 via lead 23 to be distributed to the capacitor banks as needed. It is to be understood that one or both of switches 24,26 are on during charging. Both switches 24 and 26 may be on together or only one may be on, but at least one must be on during charging. When one or both of switches 24, 26 is on, the charge on capacitor 20 is coupled to the respective one or both of capacitor banks 40, 42.

As previously stated, the value of capacitor 20 is preferably chosen to be able to absorb and store the energy from one pulse. The energy stored in capacitor 20, which is now in the form of a DC level with a generally triangular ripple component, is available to be delivered to either capacitor bank via charge switches 24 or 26. It is also to be understood that the capacitor banks include slower acting diodes (illustrated as D1 et seq. in FIG. 3 of U.S. Pat. No. 5,405,361, the disclosure of which is hereby incorporated by reference). Thus the pulse provided by transformer 14 is not instantly applied to the capacitors and the energy that is not immediately applied is stored in capacitor 20 and continues to be delivered between pulses from generator 12.

The present invention also includes voltage monitoring circuits 43, 45 for monitoring the voltage on capacitor banks 40 and 42, respectively. As can be seen in FIG. 1, monitor circuits 43 and 45 are connected to the respective capacitor banks and charge control circuit. Monitoring circuits 43 and 45 are illustrated schematically as block diagrams because there are many different embodiments of monitoring circuits that may be used without departing from the spirit or scope of the present invention, such as analog circuitry, digital circuitry and solid state components, for example. FIG. 3 illustrates one preferred embodiment of monitoring circuit 43. It should be noted that monitoring circuit 45 is the same as monitoring circuit 43. As can be seen, an operational amplifier 60 is provided as is an analog to digital converter 62 and a microprocessor 64. Amplifier 60 is connected to capacitor bank 40 via a plurality of resistors 66. In operation, monitoring circuit 43 has a database of preset values stored in microprocessor 64. When capacitor bank 40 reaches the preset value selected in processor 64, charge control circuit 28 is instructed to halt the charging of capacitor bank 40. In an alternative embodiment of the present invention, microprocessor 64 has the capability of computing an appropriate predetermined value for charging the respective capacitor bank.

When the present invention is in the charging mode, one or a plurality of capacitor banks may be charged simultaneously. In the embodiment illustrated in FIG. 1 having first and second capacitor banks 40 and 42, if both capacitor banks 40 and 42 are being simultaneously charged, when capacitor bank 42 is fully charged, charge switch 26 is opened as a result of a command from monitoring circuit 45 and all of the charge available at capacitor 20 is then applied to capacitor bank 40 instead of splitting it between the two capacitor banks. When capacitor bank 40 is completely charged, charge switch 24 is opened as a result of a command from monitoring circuit 43. Capacitor banks 40 and 42 are now fully charged and the set of individual capacitors that make up a capacitor bank are ready to be switched into series for discharge.

The invention is not to be taken as limited to all of the details thereof as modifications and variations thereof may be made without departing from the spirit or scope of the invention.

What is claimed is:

1. An apparatus for selectively charging a plurality of capacitor banks in an external defibrillator circuit comprising:

pulse generator means for generating a train of pulses;

a pulse transformer having a primary winding connected to the pulse generator means and having a secondary winding magnetically coupled to the primary winding;

low pass filter means connected to the secondary winding for filtering the train of pulses; and a pair of solid state switches, each having an input connected to the low pass filter means, and an output connected to a plurality of separate capacitor banks such that the voltage across the filter means is coupled to one of the plurality of capacitor banks when one of the plurality of switches in ON and the voltage across the filter means is uncoupled from that capacitor bank when the one switch is OFF.

2. The apparatus of claim 1 wherein the low pass filter means comprises a:

a high speed diode connected in series with a first end of the secondary winding of the pulse transformer; and a filter capacitor connected to the high speed diode and a second end of the secondary winding and having sufficient capacitance to act as a low-pass filter for the train of pulses delivered from the pulse generator means by the pulse transformer.

3. The apparatus of claim 2 wherein the voltage across the filter capacitor is coupled to at least one of the plurality of the capacitor banks when the respective at least one switch is ON and the voltage across the filter capacitor is uncoupled from the at least one capacitor bank when the respective at least one switch is OFF.

4. The apparatus of claim 1 wherein the low pass filter means comprises an active filter.

5. The apparatus of claim 1 further comprising means for controlling each of the plurality of solid state switches such that all of the switches are ON simultaneously.

6. The apparatus of claim 5 further comprising a plurality of monitoring means connected to the plurality of capacitor banks and to the means for controlling the plurality of solid state switches for monitoring the voltage levels in the respective capacitor banks.

7. The apparatus of claim 1, further comprising means for controlling each of the plurality of solid state switches such that at least one of the switches is ON while at least one of the switches is OFF.

8. The apparatus of claim 6 wherein the plurality of monitoring means are setable to store desired cut off voltage levels.

9. The apparatus of claim 1 wherein at least one of the plurality of solid state switches is an SCR.

10. The apparatus of claim 1 wherein at least one of the plurality of solid state switches is an FET.

11. The apparatus of claim 1 wherein at least one of the plurality of solid state switches is an IGBT.

12. A circuit for selectively charging at least one capacitor bank in a defibrillator, the circuit comprising:

a pulse generator for generating a train of pulses;

a pulse transformer having a primary winding connected to the pulse generator and having a secondary winding magnetically coupled to the primary winding;

a low pass filter having an input and an output wherein the input of the filter is connected to the secondary winding of the pulse transformer;

at least one charge switch having an input and an output wherein the input of the at least one charge switch is connected to the output of the low pass filter; and at least one capacitor bank connected to the output of the at least one charge switch.

13. The circuit as in claim 12 wherein the low pass filter comprises a:

a high speed diode connected in series with a first end of the secondary winding of the pulse transformer; and a filter capacitor connected to the high speed diode and a second end of the secondary winding and having sufficient capacitance to act as a low-pass filter for the train of pulses delivered from the pulse generator means by the pulse transformer.

14. The circuit as in claim 13 wherein the low pass filter comprises an active filter.

15. The circuit as in claim 13 further comprising at least one charge control circuit connected to the output of the low pass filter and the input of the at least one charge switch.

16. The circuit as in claim 15 further comprising at least one monitoring circuit connected to the at least one capacitor bank and the at least one charge control circuit.

17. The circuit as in claim 16 wherein the at least one monitoring circuit is setable to store desired cut off voltage levels for the at least one capacitor bank.

18. A method of charging a first and second capacitor bank in a biphasic external defibrillator, the method comprising the steps of:

generating a series of high frequency pulses;

rectifying and filtering the series of high frequency pulses;

selectively coupling the rectified and filtered series of high frequency pulses to a first capacitor bank via a first solid state switch in the ON condition, while simultaneously coupling the rectified and filtered series of high frequency pulses to a second capacitor bank via a second solid state switch in the ON condition.

19. The method of claim 18 further comprising the additional steps of:

monitoring the voltage levels of the capacitor banks with a monitoring circuit; and turning the first switch OFF to decouple the first capacitor bank to the rectified and filtered series of high frequency pulses when the voltage level of the first capacitor bank reaches a predetermined level set in the monitoring circuit while the second switch remains ON.

20. The method of claim 18 wherein the rectifying of step b) is performed by a fast recovery diode.

21. The method of claim 18 wherein the first and second solid state switches are SCR'S.

22. The method of claim 18 wherein the first and second solid state switches are FET's.

23. The method of claim 18 wherein the first and second solid state switches are IGBT's.

* * * * *

UNITED STATES PATENT AND TRADEMARK OFFICE
CERTIFICATE OF CORRECTION

PATENT NO. : 5,836,972
DATED : November 17, 1998
INVENTOR(S) : Gary B. Stendahl, James E. Brewer It is certified that error appears in the above-identified patent and that said Letters Patent is hereby corrected as shown below:

Column 2, line 45, please delete the word "are" and replace with the word "is".

Column 3, line 23, please change the word "increase" to the word "increases".

Column 3, line 67, Please add a "," after the word "seen" and delete the word "in" from the sentence.

Column 5, line 32, please delete the "a" and change to "comprises:".

Column 6, line 17, please delete the "a" and change to "comprises:".

Signed and Sealed this

Twenty-seventh Day of April, 1999

*Attest:*

Q. TODD DICKINSON

*Attesting Officer*  *Acting Commissioner of Patents and Trademarks*